(12) United States Patent
Yoshida et al.

(10) Patent No.: US 10,494,414 B2
(45) Date of Patent: Dec. 3, 2019

(54) IMMUNOGLOBULIN G-BINDING PEPTIDE

(71) Applicant: KANEKA CORPORATION, Osaka-shi, Osaka (JP)

(72) Inventors: Shinichi Yoshida, Takasago (JP); Dai Murata, Takasago (JP)

(73) Assignee: KANEKA CORPORATION, Osaka-shi (JP)

( * ) Notice: Subject to any disclaimer, the term of this patent is extended or adjusted under 35 U.S.C. 154(b) by 149 days.

(21) Appl. No.: 15/501,320

(22) PCT Filed: Aug. 27, 2015

(86) PCT No.: PCT/JP2015/074215
§ 371 (c)(1),
(2) Date: Feb. 2, 2017

(87) PCT Pub. No.: WO2016/031909
PCT Pub. Date: Mar. 3, 2016

(65) Prior Publication Data
US 2018/0044401 A1    Feb. 15, 2018

(30) Foreign Application Priority Data

Aug. 28, 2014  (JP) ................ 2014-174073

(51) Int. Cl.
| | | |
|---|---|---|
| *A61K 39/00* | (2006.01) | |
| *A61K 39/38* | (2006.01) | |
| *A61K 39/02* | (2006.01) | |
| *C07K 14/735* | (2006.01) | |
| *C07K 16/00* | (2006.01) | |

(52) U.S. Cl.
CPC ........ *C07K 14/70535* (2013.01); *C07K 16/00* (2013.01); *C07K 2317/55* (2013.01)

(58) Field of Classification Search
CPC .................................................... A61K 39/00
USPC ....... 424/184.1, 185.1, 234.1; 536/23.1, 23.7
See application file for complete search history.

(56) References Cited

U.S. PATENT DOCUMENTS

| | | |
|---|---|---|
| 5,965,390 A | 10/1999 | Björck et al. |
| 6,663,862 B1 | 12/2003 | Hellinga et al. |
| 2003/0027283 A1 | 2/2003 | Bjorck et al. |
| 2014/0220017 A1 | 8/2014 | Kontermann et al. |
| 2016/0289306 A1 | 10/2016 | Yoshida et al. |

FOREIGN PATENT DOCUMENTS

| | | |
|---|---|---|
| JP | 7-506573 A | 7/1995 |
| JP | 2009-195184 A | 9/2009 |
| JP | 2009-297018 A | 12/2009 |
| WO | WO 98/01560 A1 | 1/1998 |
| WO | WO 2013/041730 A1 | 3/2013 |
| WO | WO 2015/030094 A1 | 3/2015 |

OTHER PUBLICATIONS

Boström et al., "Purification Systems Based on Bacterial Surface Proteins", Protein Purification (ISBN: 978-953-307-831-1), 2012, pp. 89-136.
International Search Report for PCT/JP2015/074215 dated Dec. 1, 2015.
Nezlin et al., "Interactions of Immunoglobulins Outside the Antigen-Combining Site", Advances In Immunology, 2004, vol. 82, pp. 155-215.
Svensson et al., "The ultimate Ig-binding protein", Biajournal, 1999, No. 2, pp. 21-23.
Written Opinion of the International Searching Authority for PCT/JP2015/074215 (PCT/ISA/237) dated Dec. 1, 2015.

*Primary Examiner* — Rodney P Swartz
(74) *Attorney, Agent, or Firm* — Birch, Stewart, Kolasch & Birch, LLP

(57) ABSTRACT

The objective of the present invention is to provide a peptide of which both of binding forces to a Fc region and a Fab region are superior. In addition, the objective of the present invention is to provide a DNA which encodes the peptide, a vector which contains the DNA, and a transformant which is transformed by the vector. The problem can be solved by providing the peptide having the specific sequence.

19 Claims, 3 Drawing Sheets
Specification includes a Sequence Listing.

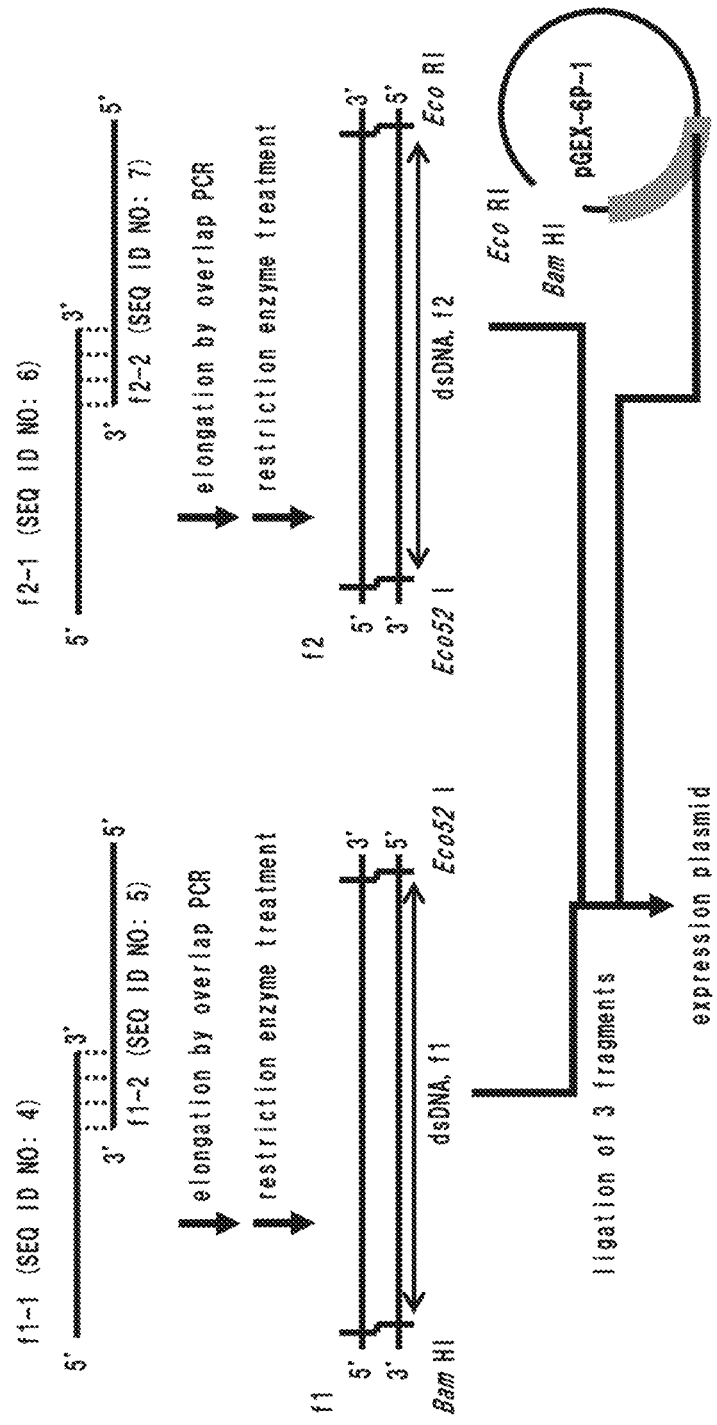
[Figure 1]

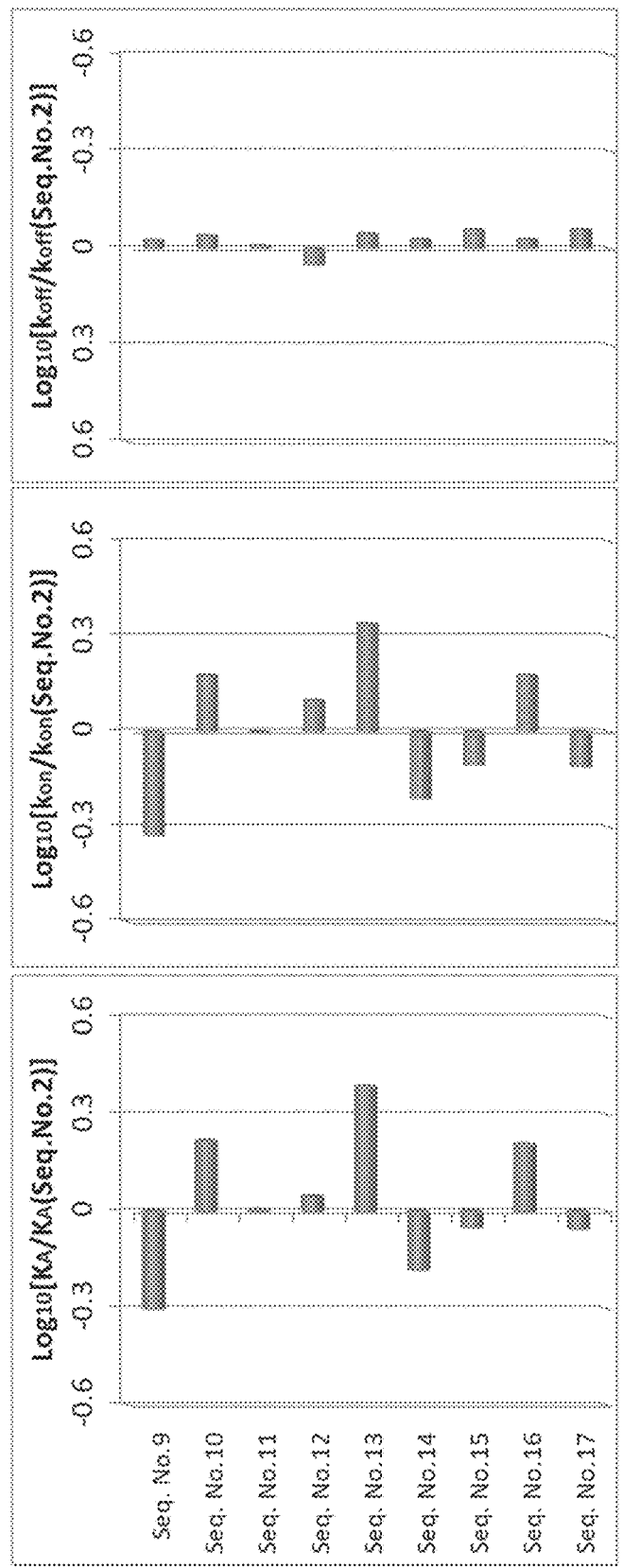
[Figure 2]

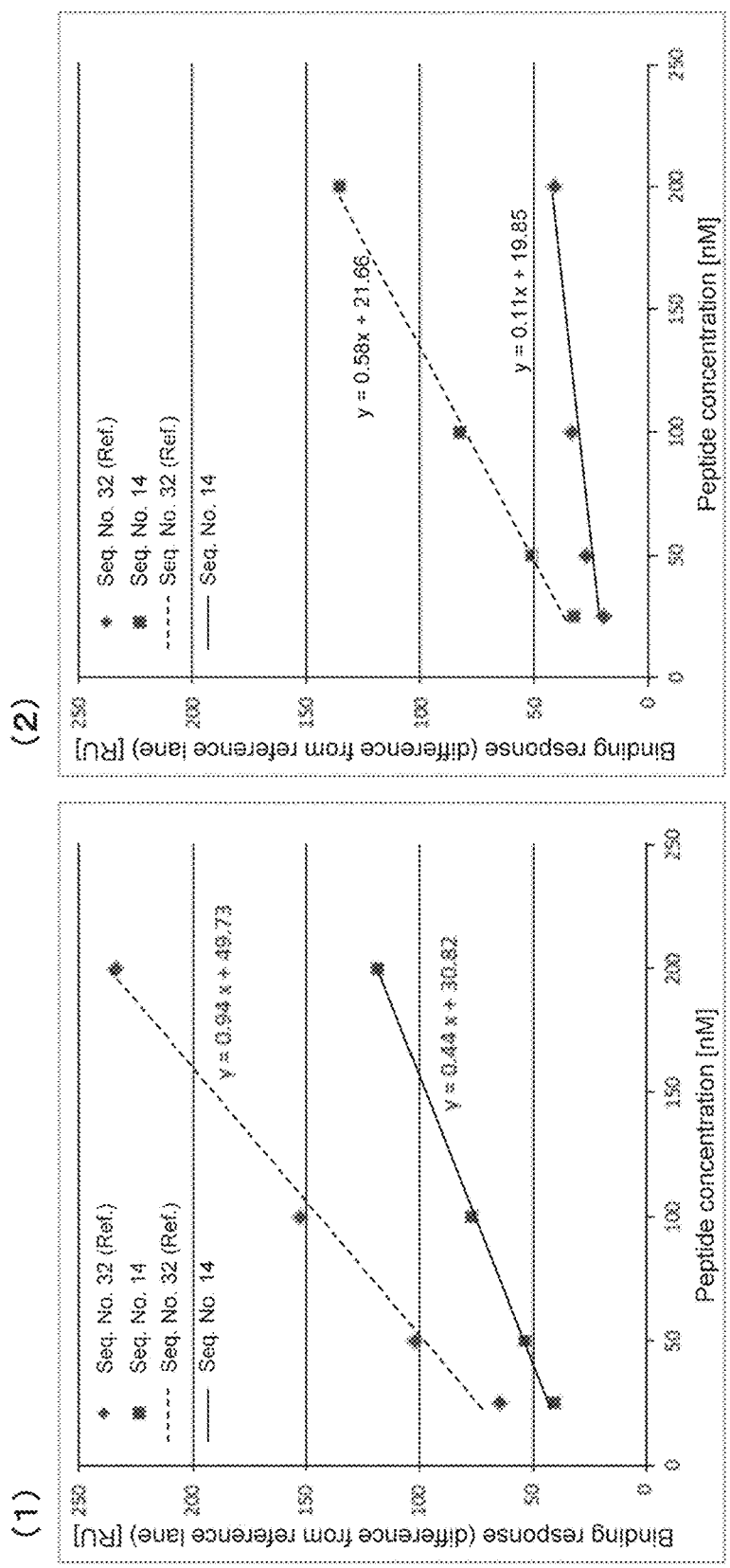
[Figure 3]

IMMUNOGLOBULIN G-BINDING PEPTIDE

REFERENCE TO SEQUENCE LISTING SUBMITTED VIA EFS-WEB

This application is being filed electronically via EFS-Web and includes an electronically submitted sequence listing in .txt format. The .txt file contains a sequence listing entitled "2017-06-28 SequenceListing 4991-0175PUS1.txt" created on Jun. 27, 2017 and is 16,911 bytes in size. The sequence listing contained in this .txt file is part of the specification and is hereby incorporated by reference herein in its entirety.

TECHNICAL FIELD

The present invention relates to an immunoglobulin G-binding peptide which has a superior ability to bind to both of a Fc region and a Fab region of an immunoglobulin G, a DNA which encodes the peptide, a vector which contains the DNA, and a transformant which is transformed by the vector.

BACKGROUND ART

As one of important functions of a protein, a capability to specifically bind to a specific molecule is exemplified. Such a capability plays an important role in an immunoreaction and signal transduction in a living body. A technology utilizing the capability has been developed for various purposes such as treatment and examination. An antibody can be exemplified as a protein which specifically binds to a specific molecule and which is one of particularly industrially utilized proteins. In addition, a protein which specifically binds to various antibodies in a manner except for an antigen-antibody reaction is also very industrially valuable, since such a protein can be used for detecting and purifying an antibody.

An industrially applicable antibody is basically an immunoglobulin G, i.e. IgG. As a IgG-binding protein, a cell wall protein of bacteria, such as Protein A, Protein G, Protein H and Protein L, has been well-known (Non-patent Document 1). Protein A is produced by gram-negative bacteria *Staphylococcus aureus*, and is a protein which binds to a Fc region of IgG. Protein G is produced by *Streptococcus* sp. classified into Group G, and is a protein which binds to a Fc region of IgG. Protein H is also produced by *Streptococcus pyogenes* classified into Group G as one of *Streptococcus*, and is a protein which binds to a Fc region of IgG. Protein L is produced by *Peptostreptococcus* spp., and is a protein which binds to a Fab region of IgG. Each protein contains a plurality of IgG-binding domains having 100 or less amino acid residues.

Recently, an antibody fragment which has a molecular structure of fragmented immunoglobulin G has been actively developed as a reagent for study use and clinical use. An immunoglobulin-binding protein which has a binding capability different from the above-described protein is also useful. For example, an immunoglobulin-binding protein which can bind to both of a Fc region and a Fab region is useful. It has been known that Protein A also binds to a Fab region; however, the Fab region to which Protein A can bind is only a Fab region of immunoglobulin G classified into the specific subfamily of VH germ cell gene, and the binding force to a Fab region is not strong in comparison with that to a Fc region (Non-patent Documents 1 and 2). It is known that Protein G binds to a Fab region though the binding force is weak; however, the association constant ($K_A$) of Protein G to a Fab region is 10 times less than that to a Fc region (Non-patent Documents 1 and 2). As a protein which binds to both of a Fc region and a Fab region, a hybrid protein produced by coupling IgG-binding domains of Protein G or Protein A and Protein L has been developed (Patent Document 1 and Non-patent Document 3). However, such a protein leaves something to be desired in terms of versatility, since Protein L has a binding activity only to the Fab region consisting of κ chain.

PRIOR ART DOCUMENT

Patent Document

Patent Document 1: JP H7-506573 T

Non-Patent Document

Non-patent Document 1: Nezlin R. et al., "Adv. Immunol.", 2004, vol. 82, pp. 155-215
Non-patent Document 2: Bostrom T. et al., "Protein Purification" (ISBN: 978-953-307-831-1), 2012, pp. 89-136
Non-patent Document 3: Svensson H. et al., "BIAJOURNAL", 1999, vol. 2, pp. 21-23

DISCLOSURE OF THE INVENTION

Problems to be Solved by the Invention

As described above, a hybrid protein produced by coupling a domain having a binding capability to a Fc region with a domain having a binding capability to a Fab region is exemplified as an immunoglobulin G-binding protein having a binding capability to both of a Fc region and a Fab region. However, in the case where already-known domains are merely bound to each other, there is a problem with the stability of a linker sequence for binding against a protease or the like. Accordingly, an immunoglobulin G-binding protein of which one domain has a binding capability to both of a Fc region and a Fab region is required. However, it is hard to say that Protein A and Protein G meet the needs in that the proteins have a binding capability to both of a Fc region and a Fab region but the binding capability thereof to a Fab region is particularly low and is limited to the specific sequence.

Under the above-described circumstances, the objective of the present invention is to provide a peptide of which both of binding forces to a Fc region and a Fab region are superior. In addition, the objective of the present invention is to provide a DNA which encodes the peptide, a vector which contains the DNA, and a transformant which is transformed by the vector.

Means for Solving the Problems

In order to solve the above-described problem, the inventors of the present invention designed an amino acid sequence which is expected to bind to both of a Fc region and a Fab region on the basis of the IgG-binding domain of Protein G, actually obtained a peptide having the amino acid sequence, evaluated the peptide, and designed again an amino acid sequence by feedback of the result. By repeating the above-described cycle, the inventors invented the IgG-binding peptide of which binding force as association constants ($K_A$) to both of a Fc region and a Fab region of an immunoglobulin G are $10^6$ [1/M] or more.

Hereinafter, the present invention completed as a result is described.

[1] An immunoglobulin G-binding peptide, comprising the following amino acid sequence (SEQ ID NO: 1) or an amino acid sequence having a sequence identity of 95% or more with the following amino acid sequence:

(SEQ ID NO: 1)
Xaa$_1$-Xaa$_2$-Tyr-Lys-Leu-Xaa$_6$-Xaa$_7$-Asn-Gly-Xaa$_{10}$-Thr-

Leu-Thr-Gly-Tyr-Thr-Thr-Ala-Ile-Ala-Xaa$_{21}$-Asp-Ala-

Xaa$_{24}$-Thr-Ala-Glu-Xaa$_{28}$-Xaa$_{29}$-Leu-Xaa$_{31}$-Gln-Phe-

Ala-Asn-Asp-Asn-Gly-Xaa$_{39}$-Xaa$_{40}$-Gly-Xaa$_{42}$-Trp-Thr-

Tyr-Asp-Xaa$_{47}$-Ala-Thr-Lys-Thr-Phe-Thr-Val-Thr-Xaa$_{56}$

Xaa$_1$=Ala, Asp, Glu, Gly, His, Ile, Lys, Leu, Met, Asn, Gln, Arg, Ser, Thr or Val
Xaa$_2$=Thr or Arg
Xaa$_6$=Ile or Val
Xaa$_7$=Leu or Ile
Xaa$_{10}$=Lys or Arg
Xaa$_{21}$=Asp, Ala or Pro
Xaa$_{24}$=Ala or Glu
Xaa$_{28}$=Lys, Ile or Arg
Xaa$_{29}$=Val or Ala
Xaa$_{31}$=Lys or Arg
Xaa$_{39}$=Val or Ile
Xaa$_{40}$=Asp or Glu
Xaa$_{42}$=Glu, Val or Met
Xaa$_{47}$=Asp, Ala or Pro
Xaa$_{56}$=Ala, Asp, Glu, Gly, His, Ile, Lys, Leu, Met, Asn, Gln, Arg, Ser, Thr or Val.

[2] The immunoglobulin G-binding peptide according to the above [1], wherein Xaa$_2$ is Thr.

[3] The immunoglobulin G-binding peptide according to the above [1] or [2], wherein Xaa$_6$ is Ile.

[4] The immunoglobulin G-binding peptide according to any one of the above [1] to [3], wherein Xaa$_7$ is Leu.

[5] The immunoglobulin G-binding peptide according to any one of the above [1] to [4], wherein Xaa$_{24}$ is Ala.

[6] The immunoglobulin G-binding peptide according to any one of the above [1] to [5], wherein Xaa$_{29}$ is Val.

[7] The immunoglobulin G-binding peptide according to any one of the above [1] to [6], wherein Xaa$_{31}$ is Lys.

[8] The immunoglobulin G-binding peptide according to any one of the above [1] to [7], wherein Xaa$_{40}$ is Asp.

[9] The immunoglobulin G-binding peptide according to any one of the above [1] to [8], wherein Xaa$_{42}$ is Glu.

[10] A DNA, encoding the peptide according to any one of the above [1] to [9].

[11] A vector, comprising the DNA according to the above [10].

[12] A transformant, transformed by the vector according to the above [11].

Effect of the Invention

The immunoglobulin G-binding peptide according to the present invention has a binding force to both of a Fc region and a Fab region of an immunoglobulin G of $10^6$ [1/M] or more as association constant ($K_A$), and has a superior binding capability to an immunoglobulin G. For example, when full length IgG is mixed with a fragmented IgG and when the structure of a target IgG is unknown, a peptide which can bind to both of a Fc region and a Fab region can be effectively utilized for detecting and purifying IgG. The immunoglobulin G-binding peptide according to the present invention is therefore useful as a general-purpose tool to provide a new solution for detecting and purifying IgG or a derivative thereof.

BRIEF DESCRIPTION OF THE DRAWINGS

FIG. 1 represents a method for preparing an expression plasmid of the immunoglobulin G-binding peptide having the amino acid sequence of SEQ ID NO: 2.

FIG. 2 are graphs of logarithmic values of binding parameters of the immunoglobulin G-binding peptides having the amino acid sequences of SEQ ID Nos: 9 to 17 in comparison with the immunoglobulin G-binding peptide having the amino acid sequences of SEQ ID No: 2.

FIG. 3 are graphs in which binding responses of the immunoglobulin G-binding peptides to a IgG-Fc and a IgG-Fab are plotted in the vertical axis and peptide concentrations are plotted in the horizontal axis from the result of the affinity property measured by using a biosensor utilizing surface plasmon resonance.

MODE FOR CARRYING OUT THE INVENTION

The term "peptide" in the present invention includes all of molecules having a peptide structure. The immunoglobulin G-binding peptide according to the present invention may be generally referred to as a "protein" or a "domain" of a protein on the basis of the number of the amino acids which constitute the essential structure thereof.

The term "immunoglobulin" is a glycoprotein produced by a B cell of a lymphocyte and has a function to recognize a molecule such as a specific protein to be bound. An immunoglobulin has not only a function to specifically bind to a specific molecule, i.e. antigen, but also a function to detoxify and remove an antigen-containing factor in cooperation with other biological molecule or cell. An immunoglobulin is generally referred to as "antibody", and the name is inspired by such functions. All of immunoglobulins basically have the same molecular structure. The basic structure of an immunoglobulin is a Y-shaped four-chain structure consisting of two light chains and two heavy chains of polypeptide chains. A light chain (L chain) is classified into two types of λ chain and κ chain, and all of immunoglobulins have either of the types. A heavy chain (H chain) is classified into five types of γ chain, μ chain, α chain, δ chain and ε chain, and an immunoglobulin is classified into isotypes depending on the kind of a heavy chain. An immunoglobulin G (IgG) is a monomer immunoglobulin, is composed of two heavy chains (γ chains) and two light chains, and has two antigen-binding sites.

A lower half vertical part in the "Y" shape of an immunoglobulin is referred to as a "Fc region", and an upper half "V" shaped part is referred to as a "Fab region". A Fc region has an effector function to initiate a reaction after binding of an antibody to an antigen, and a Fab region has a function to bind to an antigen. A Fab region and Fc region of a heavy chain are bound to each other through a hinge part. Papain, which is a proteolytic enzyme and which is contained in papaya, decomposes a hinge part to cut into two Fab regions and one Fc region. The part close to the end of the "Y" shape in a Fab region is referred to as a "variable region (V region)", since there are various changes in an amino acid sequence in order to bind to various antigens. A variable region of a light chain is referred to as a "VL region", and a variable region of a heavy chain is referred to as a "VH region". A Fc region and the other part in a Fab region except for a V region are referred to as a "constant region (C region)", since there is relatively less change. A constant region of a light chain is referred to as a "CL region", and a constant region of a heavy chain is referred to as a "CH region". A CH region is further classified into three regions of CH1 to CH3. A Fab region of a heavy chain is composed of a VH region and CH1, and a Fc region of a heavy chain is composed of CH2 and CH3. There is a hinge part between CH1 and CH2. More specifically, SpG-β binds to a CH1 region (CH1γ) and a CL region of IgG, and particularly to a CH1 region mainly (Derrick J. P., Nature, 1992, vol. 359, pp. 752-754).

The IgG-binding peptide according to the present invention is characterized in comprising the following amino acid sequence (SEQ ID NO: 1) or an amino acid sequence having a sequence identity of 90% or more with the following amino acid sequence.

(SEQ ID NO: 1)
Xaa$_1$-Xaa$_2$-Tyr-Lys-Leu-Xaa$_6$-Xaa$_7$-Asn-Gly-Xaa$_{10}$-Thr-

Leu-Thr-Gly-Tyr-Thr-Thr-Ala-Ile-Ala-Xaa$_{21}$-Asp-Ala-

Xaa$_{24}$-Thr-Ala-Glu-Xaa$_{28}$-Xaa$_{29}$-Leu-Xaa$_{31}$-Gln-Phe-

Ala-Asn-Asp-Asn-Gly-Xaa$_{39}$-Xaa$_{40}$-Gly-Xaa$_{42}$-Trp-Thr-

Tyr-Asp-Xaa$_{47}$-Ala-Thr-Lys-Thr-Phe-Thr-Val-Thr-Xaa$_{56}$

Xaa$_1$=Ala, Asp, Glu, Gly, His, Ile, Lys, Leu, Met, Asn, Gln, Arg, Ser, Thr or Val
Xaa$_2$=Thr or Arg
Xaa$_6$=Ile or Val
Xaa$_7$=Leu or Ile
Xaa$_{10}$=Lys or Arg
Xaa$_{21}$=Asp, Ala or Pro
Xaa$_{24}$=Ala or Glu
Xaa$_{28}$=Lys, Ile or Arg
Xaa$_{29}$=Val or Ala
Xaa$_{31}$=Lys or Arg
Xaa$_{39}$=Val or Ile
Xaa$_{40}$=Asp or Glu
Xaa$_{42}$=Glu, Val or Met
Xaa$_{47}$=Asp, Ala or Pro
Xaa$_{56}$=Ala, Asp, Glu, Gly, His, Ile, Lys, Leu, Met, Asn, Gln, Arg, Ser, Thr or Val.

The amino acid sequence of the immunoglobulin G-binding peptide according to the present invention may contain the amino acid sequence of SEQ ID NO: 1 or an amino acid sequence having a sequence identity of 95% or more with the amino acid sequence of SEQ ID NO: 1, or may contain other amino acid sequence in addition to the above amino acid sequences. In addition, other compound may bind to the amino acid sequences. For example, such other amino acid sequence is exemplified by a linker peptide for binding each domain in a peptide multimer described later, other peptide having a different function, and a linker peptide for binding the present invention peptide to a water-insoluble carrier. However, it is preferred that the amino acid sequence of the immunoglobulin G-binding peptide according to the present invention consists of the amino acid sequence of SEQ ID NO: 1 or an amino acid sequence having a sequence identity of 95% or more with the amino acid sequence of SEQ ID NO: 1. Even in such cases, the immunoglobulin G-binding peptide according to the present invention may be immobilized on a water-insoluble carrier through a linker group. In addition, the immunoglobulin G-binding peptides may be bound to each other through a linker group in the case of a multimer.

The immunoglobulin G-binding peptide according to the present invention has excellent binding capability to an immunoglobulin G (IgG). Specifically, each binding force to a Fc region and a Fab region of an immunoglobulin G is $10^6$ [1/M] or more as an association constant, i.e. $K_A$.

For example, the binding force, i.e. affinity, of the IgG-binding peptide according to the present invention to a Fc region and a Fab region of an immunoglobulin G can be evaluated by using a biosensor such as Biacore system (manufactured by GE Healthcare Bioscience) utilizing surface plasmon resonance principle; however, the means is not restricted thereto.

With respect to a condition for measuring a binding capability to a Fc region and a Fab region of an immunoglobulin G, binding signals at the time of binding to each of a Fc region and a Fab region of an immunoglobulin G may be detected. For example, the binding capability can be easily measured at a constant temperature of 20 to 40° C. and in a neutral condition of pH 6 to 8.

An immunoglobulin G molecule as a binding partner is not restricted as long as a binding to a Fc region or a Fab region can be detected. However, it is preferred to use a fragmented IgG having only either of a Fc region or a Fab region, since it is difficult to distinguish the bindings to the two regions from each other to be detected when an immunoglobulin G having both of the regions is used.

For example, as a binding parameter, association constant ($K_A$) and dissociation constant ($K_D$) can be used (Nagata et al., "Real-Time Analysis Experimental Method for Interaction Between Biological Substances", Springer-Verlag Tokyo, 1998, p. 41). An association constant between the present invention peptide and a Fc fragment or a Fab fragment can be measured by immobilizing a Fc fragment or a Fab fragment on a sensor tip and adding the present invention peptide into a flow channel under a condition of the temperature of 25° C. and pH 7.4 in Biacore system.

In an experiment utilizing Biacore system, the order of a parameter may be largely changed depending on an experimental condition, an analysis method and/or the kind of used original IgG. Under such a circumstance, when an evaluation is also conducted by using a wild Protein G in the same experimental condition and analysis method, it becomes standard whether the measured association constant is larger or not in comparison with the association constant of wild Protein G to a Fab region. The performance of a conventional wild Protein G is not sufficient as a peptide which binds to both of a Fc region and a Fab region of an immunoglobulin G, since the binding force thereof to a Fab region is not sufficient. The present invention is importantly characterized in exhibiting much superior binding capability to a Fab region in comparison with a binding capability of wild Protein G to a Fab region. A wild Protein G is easily available as a commercial reagent for study. For example, such a commercial reagent is manufactured by Life Technologies Corporation. Alternatively, a peptide having an amino acid sequence of a IgG-binding domain of Protein G described in FIG. 5 of Non-patent Document 2 may be prepared. When an association constant $K_A$ of wild Protein G to a Fab fragment is measured and analyzed in the above-described condition, the value is about $10^5$ as an order.

The association constant $K_A$ of the IgG-binding peptide according to the present invention to a Fc fragment is $10^6$ or more as an order, and the association constant $K_A$ to a Fab fragment is also $10^6$ or more as an order. It is more preferred that the order of the association constant to a Fc fragment is the same as the order of the association constant to a Fab fragment. From another point of view, it is even more preferred that the association constant to a Fab fragment is larger than the association constant to a Fc fragment to an extent not exceeding 10 times.

With respect to the IgG-binding peptide according to the present invention, the sequence identity is preferably 95% or more, more preferably 96% or more, even more preferably 97% or more, and particularly preferably 98% or more. The sequence identity can be measured by a program for amino acid sequence multiple alignment, such as Clustal (www.clustal.org/omega/). Even when a part of the amino acid sequence is changed in the above-described range, a person skilled in the art can easily identify an amino acid residue which exists at a position corresponding to a specific position of the amino acid sequence of SEQ ID NO: 1.

In terms of a binding capability to a Fab region and Fc region, it is preferred that in the amino acid sequence of SEQ ID NO: 1 according to the present invention, the $2^{nd}$ position is Thr, the $6^{th}$ position is Ile, the $7^{th}$ position is Leu, the $24^{th}$ position is Ala, the $29^{th}$ position is Val, the $31^{st}$ position is Lys, the $40^{th}$ position is Asp, and the $42^{nd}$ position is Glu. In addition, it is also preferred that the $13^{th}$ position is Thr, the $15^{th}$ position is Tyr, the $19^{th}$ position is Ile, the $30^{th}$ position is Leu and/or the $33^{rd}$ position is Phe.

In the present invention, one or several amino acids may be added to the above-described amino acid sequence of the IgG-binding peptide according to the present invention as one of the embodiments.

The position of the addition is preferably the N-terminal and C-terminal. The above-described range of "one or several" may be, for example, 1 or more and 30 or less, preferably 1 or more and 20 or less, more preferably 1 or more and 10 or less, even more preferably 1 or more and 7 or less, even more preferably 1 or more and 5 or less, and particularly preferably 1 or more and 3 or less, 1 or 2, or 1. In any cases, the peptide having the amino acid sequence according to the present invention is included in the range of the present invention, and the peptide having the present invention sequence without the N-terminal or C-terminal amino acid, i.e. $Xaa_1$ or $Xaa_{56}$, is included in the range of the present invention as one of the embodiments.

As one of the embodiments, the IgG-binding peptide according to the present invention may be a multimer of 2 or more domains connected each other, preferably 3 or more domains, more preferably 4 or more domains, and even more preferably 5 or more domains. A domain monomer has the above-described sequence. With respect to the upper limit of the number of connected domains, 10 or less is preferred, 8 or less is more preferred, and 6 or less is even more preferred. Such a domain multimer may be a homopolymer in which one kind of Fab region-binding peptides are connected, such as homodimer and homotrimer, or a heteropolymer in which two or more kinds of Fab region-binding peptides are connected, such as heterodimer and heterotrimer.

A method for connecting monomer proteins according to the present invention is exemplified by a connecting method through one or more amino acid residues and a method for directly connecting the monomer proteins without using an amino acid residue; however, is not restricted to the exemplified methods. The number of the amino acid residue for connection is not particularly restricted, and is preferably 20 residues or less, more preferably 15 residues or less, even more preferably 10 residues or less, even more preferably 5 residues or less, and even more preferably 2 residues or less. From another point of view, it is preferred that the amino acid residue for connection does not destabilize a three dimensional structure of the monomer protein.

As one embodiment, a fusion peptide prepared by fusing the IgG-binding peptide according to the present invention as one structural component with other peptide having different function is exemplified. Such a fusion peptide is exemplified by a peptide fused with albumin or GST, i.e. glutathione S-transferase, but is not restricted to the examples. In addition, peptides fused with a nucleic acid such as DNA aptamer, a drug such as antibiotic or a polymer such as PEG, i.e. polyethylene glycol, are also included in the range of the present invention as long as such a fusion peptide utilizes the utility of the present invention peptide.

It is also included in the range of the present invention as one embodiment to use the above-described present invention peptide as an affinity ligand having an affinity for an immunoglobulin or a fragment thereof. An affinity separation matrix prepared by immobilizing the ligand on a water-insoluble carrier is similarly included in the range of the present invention as one embodiment. The term "affinity ligand" in the disclosure means a substance and a functional group to selectively bind to and adsorb a target molecule from an aggregate of molecules on the basis of a specific affinity between molecules, such as binding between an antigen and an antibody. In the present invention, the term "affinity ligand" means the peptide which specifically binds to an immunoglobulin G or a fragment thereof. In the present invention, the term "ligand" also means an "affinity ligand".

The water-insoluble carrier usable in the present invention is exemplified by an inorganic carrier such as glass beads and silica gel; a synthetic polymer such as cross-linked polyvinyl alcohol, cross-linked polyacrylate, cross-linked polyacrylamide and cross-linked polystyrene; an organic carrier composed of a polysaccharide, such as crystalline cellulose, cross-linked cellulose, cross-linked agarose and cross-linked dextran; and a composite carrier obtained from the combination of the above carriers, such as an organic-organic composite carrier and an organic-inorganic composite carrier. The commercial product thereof is exemplified by porous cellulose gel GCL2000, Sephacryl (registered trademark) S-1000 prepared by crosslinking allyl dextran and methylene bisacrylamide with a covalent bond, an acrylate carrier Toyopearl (registered trademark), a cross-linked agarose carrier Sepharose (registered trademark) CL4B, and a cross-linked cellulose carrier Cellufine (registered trademark). However, it should be noted that the water-insoluble carrier usable in the present invention is not restricted to the carriers exemplified as the above.

It is preferred that the water-insoluble carrier usable in the present invention has large surface area and that the carrier has a large number of fine pores with a suitable size and is porous in terms of a purpose and method for using the affinity separation matrix according to the present invention. The carrier can have any forms such as beads, monolith, fiber and film (including hollow fiber), and any forms can be selected.

With respect to a method for immobilizing the ligand, for example, the ligand can be bound to a carrier by a conventional coupling method utilizing an amino group, carboxy group or a thiol group of the ligand. Such a coupling method is exemplified by an immobilization method including activation of a carrier by a reaction with cyanogen bromide, epichlorohydrin, diglycidyl ether, tosyl chloride, tresyl chloride, hydrazine, sodium periodate or the like, or introduction of a reactive functional group into the carrier surface, and the coupling reaction between the resulting carrier and a compound to be immobilized as a ligand; and an immobilization method by condensation and crosslinking which include adding a condensation reagent such as carbodiimide or a reagent having a plurality of functional groups in the molecule, such as glutaraldehyde, into a mixture containing a carrier and a compound to be immobilized as a ligand.

A spacer molecule composed of a plurality of atoms may be introduced between the ligand and carrier. Alternatively, the ligand may be directly immobilized on the carrier. Accordingly, the Fab region-binding peptide according to the present invention may be chemically modified for immobilization, or may have an additional peptide containing 1 or more and 100 or less amino acid residues useful for immobilization as a linker group. Such an amino acid useful for immobilization is exemplified by an amino acid having a functional group useful for a chemical reaction for immobilization in a side chain, and specifically exemplified by Lys having an amino group in a side chain and Cys having a thiol group in a side chain. The number of the amino acid residue contained in the above-described peptide linker group is preferably 50 or less, more preferably 40 or less or 20 or less, and even more preferably 10 or less. Since the binding capability to a Fab region of the peptide according to the present invention is maintained in a matrix prepared by immobilizing the peptide as a ligand in the present invention, any modification and change for immobilization are included in the range of the present invention.

It becomes possible by using the affinity separation matrix of the present invention that an immunoglobulin G or a fragment thereof is purified in accordance with affinity column chromatography purification method. An immunoglobulin G and a fragment thereof can be purified by a procedure in accordance with a method for purifying an immunoglobulin by affinity column chromatography, for example, by a method using SpA affinity separation matrix (Non-Patent Document 1). Specifically, after a buffer which contains an immunoglobulin G or a fragment thereof and of which pH is approximately neutral is prepared, the solution is allowed to pass through an affinity column filled with the affinity separation matrix of the present invention so that the immunoglobulin G or fragment thereof is adsorbed. Then, an appropriate amount of a pure buffer is allowed to pass through the affinity column to wash the inside of the column. At the time, the target immunoglobulin G or fragment thereof is still adsorbed on the affinity separation matrix of the present invention in the column. The affinity separation matrix on which the peptide according to the present invention is immobilized as a ligand is excellent in the absorption and retention performance of a target immunoglobulin G or fragment thereof from the step of adding a sample through the step of washing the matrix. Then, an acid buffer of which pH is appropriately adjusted is allowed to pass through the column to elute the target immunoglobulin G or fragment thereof. As a result, purification with high purity can be achieved. Into the acid buffer for elution, a substance for promoting dissociation from the matrix may be added.

The affinity separation matrix according to the present invention can be reused by allowing an adequate strong acid or strong alkali pure buffer which does not completely impair the function of the ligand compound or the base material of the carrier to pass through the matrix for wash. As the wash solution, a solution containing an adequate modifying agent or an organic solvent may be used.

The present invention also relates to a DNA which encodes the above-described peptide. The DNA encoding the present invention peptide may be any DNA as long as the amino acid sequence produced from translation of the base sequence of the DNA constitutes the peptide. Such a base sequence can be obtained by a generally used known technologies, for example, by polymerase chain reaction (hereinafter, abbreviated as "PCR") method. Alternatively, such a base sequence can be synthesized by publicly-known chemical synthesis method or is available from DNA library. A codon in the base sequence may be substituted by a degenerate codon, and the base sequence is not necessarily the same as the original base sequence as long as the translated amino acids are the same as those encoded by the original base sequence. It is possible to obtain a recombinant DNA having the one or more base sequences, a vector containing the recombinant DNA, such as a plasmid and a phage, a transformant transformed by the vector having the DNA, a genetically engineered organism having the DNA introduced therein, or a cell-free protein synthesis system using the DNA as a template for transcription.

The IgG-binding peptide according to the present invention may be available in the form of a fusion peptide with a publicly-known protein which beneficially has an action to assist the expression of a protein or to facilitate the purification of a protein. In other words, it is possible to obtain a microorganism or cell containing at least one recombinant DNA encoding a fusion peptide containing the IgG-binding peptide according to the present invention. The above-described protein is exemplified by a maltose-binding protein (MBP) and a glutathione S-transferase (GST), but is not restricted thereto.

Site-specific mutagenesis for modifying the DNA encoding the peptide of the present invention can be carried out using recombinant DNA technology, PCR method or the like as follows.

Specifically, mutagenesis by recombinant DNA technology can be carried out as follows: for example, in the case where there are suitable restriction enzyme recognition sequences on both sides of a mutagenesis target site in the gene encoding the present invention peptide, cassette mutagenesis method can be carried out in which a region containing the mutagenesis target site is removed by cleaving the restriction enzyme recognition sites with restriction enzymes and then a mutated DNA fragment is inserted. Into the mutated DNA fragment, mutation is introduced only at the target site by a method such as chemical synthesis.

For example, site-directed mutagenesis by PCR can be carried out by double primer mutagenesis. In double primer mutagenesis, PCR is carried out by using a double-stranded plasmid encoding the present invention peptide as a template, and using two kinds of synthesized oligo primers which contain complementary mutations in the + strand and − strand.

A DNA encoding the multimer peptide can be produced by ligating the desired number of DNAs each encoding the monomer peptide (single domain) of the present invention to one another in tandem. For example, with respect to connecting method for the DNA encoding the multimer peptide, a suitable restriction enzyme site is introduced in the DNA sequence and double-stranded DNA fragments cleaved with restriction enzyme are ligated using a DNA ligase. One restriction enzyme site may be introduced or a plurality of restriction enzyme sites of different types may be introduced. When the base sequences encoding each monomer peptide in the DNA encoding the multimer peptide are the same, homologous recombination may be possibly induced in a host. Thus, the sequence identity between base sequences of DNAs encoding monomer peptides to be ligated may be 90% or less, preferably 85% or less, more preferably 80% or less, and even more preferably 75% or less. In addition, the identity of the base sequence can be also determined by an ordinary method similarly to the amino acid sequence.

The "expression vector" of the present invention contains a base sequence encoding the above-described peptide of the present invention or a part of the amino acid sequence of the peptide, and a promoter which can be operably linked to the base sequence to function in a host. In general, the expression vector can be obtained by linking or inserting a gene encoding the present invention peptide to a suitable vector. The vector into which the gene is inserted is not particularly restricted as long as the vector is capable of autonomous replication in a host. As such a vector, a plasmid DNA or a phage DNA can be used. For example, in the case of using *Escherichia coli* as a host, a pQE series vector (manufactured by QIAGEN), a pET series vector (manufactured by Merck), a pGEX series vector (manufactured by GE Healthcare Bioscience) or the like can be used.

The transformant of the present invention can be produced by introducing the recombinant vector of the present invention into a host cell. A method for introducing the recombinant DNA into a host is exemplified by a method using a calcium ion, electroporation method, spheroplast method, lithium acetate method, *agrobacterium* infection method, particle gun method and polyethylene-glycol method, but is not restricted thereto. A method for expressing the function of the obtained gene in a host is exemplified by a method in which the gene obtained by the present invention is implanted into a genome (chromosome). A host cell is not particularly restricted, and bacteria (eubacteria) such as *Escherichia coli, Bacillus subtilis, Brevibacillus, Staphylococcus, Streptococcus, Streptomyces* and *Corynebacterium* can be preferably used in terms of mass production in a low cost.

The IgG-binding peptide according to the present invention can be produced by culturing the above-described transformant in a medium to allow the cell to produce and accumulate the peptide of the present invention in the cultured bacterial cell (including the periplasmic space of the bacterial cell) or in the culture solution (outside the bacterial cell), and collecting the desired peptide from the culture. In addition, the peptide of the present invention can also be produced by culturing the above-described transformant in a medium to allow the cell to produce and accumulate a fusion protein containing the peptide of the present invention in the cultured bacterial cell (including the periplasmic space of the bacterial cell) or in the culture solution (outside the bacterial cell), collecting the fusion peptide from the culture, cleaving the fusion peptide with a suitable protease, and collecting the desired peptide.

The transformant of the present invention can be cultured in a medium in accordance with a common method for culturing a host cell. The medium used for culturing the obtained transformant is not particularly restricted as long as the medium enables high yield production of the peptide of the present invention with high efficiency. Specifically, carbon source and nitrogen source, such as glucose, sucrose, glycerol, polypeptone, meat extract, yeast extract and casamino acid, can be used. In addition, an inorganic salt such as potassium salt, sodium salt, phosphate, magnesium salt, manganese salt, zinc salt and iron salt is added as required. In the case of an auxotrophic host cell, a nutritional substance necessary for the growth thereof may be added. In addition, an antibiotic such as penicillin, erythromycin, chloramphenicol and neomycin may be added as required.

Furthermore, in order to inhibit the degradation of the target peptide caused by a host-derived protease present inside or outside the bacterial cell, a publicly-known protease inhibitor and/or other commercially available protease inhibitor may be added in an appropriate concentration. The publicly-known protease inhibitor is exemplified by phenylmethane sulfonyl fluoride (PMSF), benzamidine, 4-(2-aminoethyl)-benzenesulfonyl fluoride (AEBSF), antipain, chymostatin, leupeptin, Pepstatin A, phosphoramidon, aprotinin and ethylenediaminetetra acetic acid (EDTA).

In order to obtain rightly folded IgG-binding peptide according to the present invention, for example, a molecular chaperone such as GroEL/ES, Hsp70/DnaK, Hsp90 and Hsp104/ClpB may be used. For example, such a molecular chaperone is co-existed with the present invention peptide by coexpression or as a fusion protein. As a method for obtaining rightly folded present invention peptide, addition of an additive for assisting right folding into the medium and culturing at a low temperature are exemplified, but the method is not restricted thereto.

The medium for culturing transformant produced from an *Escherichia coli* as a host is exemplified by LB medium containing triptone 1%, yeast extract 0.5% and NaCl 1%, 2×YT medium containing triptone 1.6%, yeast extract 1.0% and NaCl 0.5%, or the like.

For example, the transformant may be aerobically cultured in an aeration-stirring condition at a temperature of 15 to 42° C., preferably 20 to 37° C., for several hours to several days. As a result, the peptide of the present invention is accumulated in the cultured cell (including the periplasmic space) or in the culture solution (outside the bacterial cell) to recover the peptide. In some cases, the culturing may be performed anaerobically without aeration. In the case where a recombinant peptide is secreted, the produced recombinant peptide can be recovered after the culture period by separating the cultured cell and the supernatant containing the secreted peptide through a common separation method such as centrifugation and filtration. In addition, in the case where the peptide is accumulated in the cultured cell (including the periplasmic space), the peptide accumulated in the cell can be recovered, for example, by collecting the bacterial cell from the culture solution by centrifugation, filtration or the like, and then disrupting the bacterial cell by sonication, French press method or the like, and/or solubilizing the bacterial cell by adding a surfactant or the like.

A method for purifying the peptide of the present invention can be carried out by any one or an appropriate combination of techniques such as affinity chromatography, cation or anion exchange chromatography, gel filtration chromatography or the like. It can be confirmed whether the obtained purified substance is the target peptide or not by an ordinary method such as SDS polyacrylamide gel electrophoresis, N-terminal amino acid sequence analysis, Western blot analysis.

The present application claims the benefit of the priority date of Japanese patent application No. 2014-174073 filed on Aug. 28, 2014. All of the contents of the Japanese patent application No. 2014-174073 filed on Aug. 28, 2014, are incorporated by reference herein.

EXAMPLES

Hereinafter, the present invention is described in more detail with Examples. However, the present invention is not restricted to the following Examples.

Example 1

Preparation of IgG-Binding Peptide (1) Preparation of SpG Mutant Expression Plasmid A base sequence (SEQ ID NO: 3) encoding the peptide having the amino acid sequence of the present invention (SEQ ID NO: 2) was designed by reverse translation from the amino acid sequence. The method for producing the expression plasmid is shown in FIG. 1. A peptide-coding DNA was prepared by ligating two kinds of double-stranded DNAs (f1 and f2) having the same restriction enzyme site, and integrated into the multiple cloning site of the expression vector. In fact, the preparation of the peptide-coding DNA and the integration into the vector were simultaneously performed by ligating three fragments for connecting three double-stranded DNAs of the two kinds of double-stranded DNAs and the expression vector. The two kinds of double-stranded DNAs were prepared by elongating two kinds of single-stranded DNAs (f1-1/f1-2 or f2-1/f2-2) respectively containing about 30-base complementary region with overlapping PCR. Hereinafter, the specific experimental procedure is described. Single-stranded oligo DNAs f1-1 (SEQ ID NO: 4)/f1-2 (SEQ ID NO: 5) were synthesized by outsourcing to Sigma Genosys. The overlapping PCR was performed using Blend Taq (manufactured by TOYOBO CO., LTD.) as a polymerase. The PCR product was subjected to agarose electrophoresis and the target band was cut out. The thus extracted double-stranded DNA was cleaved with the restriction enzymes BamHI and Eco52I (both available from Takara Bio, Inc.). Similarly, single-stranded oligo DNAs f2-1 (SEQ ID NO: 6)/f2-2 (SEQ ID NO: 7) were synthesized by outsourcing. The double-stranded DNA synthesized through the overlapping PCR was extracted and cleaved with the restriction enzymes Eco52I and EcoRI (both available from Takara Bio, Inc.). Then, the two kinds of double-stranded DNAs were sub-cloned into the BamHI/EcoRI site in the multiple cloning site of the plasmid vector pGEX-6P-1 (GE Healthcare Bioscience). The ligation reaction for the subcloning was performed using Ligation high (manufactured by TOYOBO CO., LTD.) in accordance with the protocol attached to the product.

A competent cell ("*Escherichia coli* HB101" manufactured by Takara Bio, Inc.) was transformed using the above-described plasmid vector pGEX-6P-1 in accordance with the protocol attached to the competent cell product. By using the plasmid vector pGEX-6P-1, a peptide which is fused with glutathione-S-transferase (hereinafter, abbreviated as "GST") can be produced. Then, the plasmid DNA was amplified and extracted using a plasmid purification kit ("Wizard Plus SV Minipreps DNA Purification System" manufactured by Promega) in accordance with the standard protocol attached to the kit. The base sequence of the peptide-coding DNA of the expression plasmid was determined by using DNA sequencer ("3130x1 Genetic Analyzer" manufactured by Applied Biosystems). The sequencing PCR was performed by using a gene analysis kit ("BigDye Terminator v. 1.1 Cycle Sequencing Kit" manufactured by Applied Biosystems) and DNA primers for sequencing the plasmid vector pGEX-6P-1 (manufactured by GE Healthcare Bioscience) in accordance with the attached protocol. The sequencing product was purified by using a plasmid purification kit ("BigDye XTerminator Purification Kit" manufactured by Applied Biosystems) in accordance with the attached protocol and used for the base sequence analysis.

(2) Preparation of Peptide

The transformant produced by integrating the plasmid which was obtained in the above-described (1) and which expressed the peptide (SEQ ID NO: 2) was cultured in 2×YT medium containing ampicillin at 37° C. overnight. The culture liquid was inoculated in 2×YT medium containing about a 100-fold amount of ampicillin and cultured at 37° C. for about 2 hours. Then, IPTG, i.e. isopropyl-1-thio-β-D-galactoside, was added so that the final concentration thereof became 0.1 mM, and the transformant was further cultured at 37° C. for 18 hours.

After the culture, the bacterial cell was collected by centrifugation and re-suspended in 5 mL of PBS buffer. The cell was broken by sonication and centrifuged to separate a supernatant fraction as a cell-free extract and an insoluble fraction. A fusion peptide having GST added to the N-terminal is expressed by integrating a target gene into the multiple cloning site of pGEX-6P-1 vector. Each fraction was analyzed by SDS electrophoresis; as a result, a peptide band assumed to be induced by IPTG was detected at a position corresponding to a molecular weight of about 25,000 or more in the lane of the cell-free extract.

The GST fusion peptide was roughly purified from the cell-free extract containing the GST fusion peptide by affinity chromatography using a GSTrap FF column (GE Healthcare Bioscience), which had an affinity for GST. Specifically, the cell-free extract was added to the GSTrap FF column and the column was washed with a standard buffer (20 mM $NaH_2PO_4$—$Na_2HPO_4$, 150 mM NaCl, pH 7.4). Then, the target GST fusion peptide was eluted by using an elution buffer (50 mM Tris-HCl, 20 mM Glutathione, pH 8.0).

By integrating a gene into a multiple cloning site of pGEX-6P-1 vector, an amino acid sequence by which GST can be cleaved using sequence-specific protease: PreScission Protease (manufactured by GE Healthcare Bioscience) is inserted between GST and a target protein. By using such PreScission Protease, GST was cleaved in accordance with the attached protocol. The target peptide was purified from the GST-cleaved sample used for assay by gel filtration chromatography using a Superdex 75 10/300 GL column (manufactured by GE Healthcare Bioscience). The reaction mixture was added to the Superdex 75 10/300 GL column equilibrated with a standard buffer, and the target protein therein was separated and purified from the cleaved GST and PreScission Protease. The above-described all of the peptide purification by chromatography using the column was performed by using AKTAprime plus system (manufactured by GE Healthcare Bioceince). In addition, after the cleavage of GST, the peptide produced in the present Example had the sequence Gly-Pro-Leu-Gly-Ser (SEQ ID NO: 37) derived from the vector pGEX-6P-1 at the N-terminal side.

Example 2

Evaluation of Affinity of Peptide for IgG-Fc/Fab (1) Preparation Fc/Fab Fragments Derived from IgG A humanized monoclonal IgG product as a raw material was fragmented into a Fab fragment and a Fc fragment using papain, and only the Fab fragment was separated and purified. Hereinafter, a method for producing IgG-Fc/IgG-Fab derived from anti-RSV monoclonal antibody (generic name: Palivizumab) is described. The term "RSV" is an abbreviation of RS virus. In the present disclosure, when other IgG-Fc and IgG-Fab were used for evaluation, the fragments were basically prepared in a similar method.

Specifically, a humanized monoclonal IgG product ("Synagis" manufactured by CHUGAI PHARMACEUTICAL CO., LTD., in the case of anti-RS virus monoclonal agent) was dissolved in a buffer for papain treatment (0.1M AcOH—AcONa, 2 mM EDTA, 1 mM cysteine, pH 5.5), and agarose immobilized by papain ("Papain Agarose from papaya latex" manufactured by SIGMA) was added thereto. The mixture was incubated with stirring by a rotator at 37° C. for about 8 hours. The IgG-Fc was purified from the reaction mixture which contained both of a Fab fragment and a Fc fragment and which was separated from the agarose immobilized by papain by recovering the IgG-Fc as a flow-through fraction of an affinity chromatography using Kappa Select column (manufactured by GE Healthcare Bioscience). The IgG-Fab was purified by recovering the IgG-Fab as a flow-through fraction in an affinity chromatography using KanCapA column (manufactured by GE Healthcare Bioscience). The obtained crude IgG-Fc solution was subjected to purification by gel filtration chromatography using Superdex 75 10/300 GL column to obtain IgG-Fc solution. In the chromatography, a standard buffer was used for equilibration and separation. The obtained crude IgG-Fab solution was similarly subjected to purification. Similarly to the above-described Example 1, AKTAprime plus system was used in the chromatography for protein purification.

(2) Analysis of Affinity of Peptide for IgG-Fc/Fab

The affinity of the peptide obtained in the above-described Example 1(2) for the Fc region and Fab region of anti-RSV monoclonal antibody was evaluated using a biosensor Biacore3000 (manufactured by GE Healthcare Bioscience) utilizing surface plasmon resonance. In the present Example, the IgG-Fc or IgG-Fab obtained in the above-described Example 2(1) was immobilized on a sensor tip, and the peptide solution was flowed across the sensor tip to detect the interaction between the two. The IgG-Fab or IgG-Fc was immobilized on a sensor tip CM5 by amine coupling method using N-hydroxysuccinimide (NHS) and N-ethyl-N'-(3-dimethylaminopropyl)carbodiimide hydrochloride (EDC), and ethanolamine was used for blocking. All of the sensor tip and reagents for immobilization was manufactured by GE Healthcare Bioscience. The IgG-Fab solution was diluted to about 10 times using a buffer for immobilization (10 mM AcOH—AcONa, pH 4.5), and the IgG-Fab was immobilized on the sensor tip in accordance with the protocol attached to the Biacore 3000. In addition, a reference cell as negative control was also prepared by activating another flow cell on the tip with EDC/NHS and then immobilizing ethanolamine only. Peptide solutions having concentrations of 16 nM, 64 nM or 256 nM were prepared using a running buffer (20 mM $NaH_2PO_4$—$Na_2HPO_4$, 150 mM NaCl, 0.005% P-20, pH 7.4). Each peptide solution was added to the sensor tip in a flow rate of 40 μL/min for 1 minute. Bonding response curves at the time of addition (association phase, 1 minute) and after the addition (dissociation phase, 1 minute) were sequentially obtained at a measurement temperature of 25° C. After each measurement, about 20 mM NaOH was added for wash. The bonding response curve obtained by subtracting the bonding response curve of the reference cell was subjected to fitting analysis by a binding model of 1:1 using a software BIA evaluation attached to the system, and affinity constant ($K_A = k_{on}/k_{off}$) to human IgG-Fc and IgG-Fab was calculated. The analysis result is shown in Table 1.

TABLE 1

| Sequence number | | Anti-RSV antibody - Fc | | | Anti-RSV antibody - Fab | | |
|---|---|---|---|---|---|---|---|
| Amino acid sequence | cDNA sequence | $k_{on}$ ×10$^4$ M$^{-1}$s$^{-1}$ | $k_{off}$ ×10$^{-2}$ s$^{-1}$ | $K_A$ ×10$^6$ M$^{-1}$ | $k_{on}$ ×10$^4$ M$^{-1}$s$^{-1}$ | $k_{off}$ ×10$^{-2}$ s$^{-1}$ | $K_A$ ×10$^6$ M$^{-1}$ |
| 2 | 3 | 9.7 | 2.8 | 3.5 | 6.6 | 0.3 | 20.0 |

As the result shown in Table 1, it was confirmed that each binding force of the peptide according to the present invention to the Fc fragment and Fab fragment is 10$^6$ [1/M] or more as an association constant $K_A$. By the evaluation using the IgG-Fc and IgG-Fab prepared from anti-RSV monoclonal antibody, it was confirmed that the binding force to Fab is somewhat larger and the difference between the binding forces are less than 10 times as association constants. With respect to publicly-known Protein A, Protein G, and a hybrid protein thereof, the binding forces to Fc are larger than those to Fab (Non-patent Document 2). Thus, since the peptide according to the present invention exerts effect opposite to the above publicly-known proteins and has sufficient binding force to both regions, the present invention peptide has unprecedented characteristics.

(3) Evaluation of Affinity for Various IgG-Fab

Also, the affinity of the peptide according to the present invention (SEQ ID NO: 2) for IgG-Fab prepared from anti-EGFR monoclonal antibody ("Erbitux" sold by Bristol-Myers Squibb) and anti-TNFα monoclonal antibody ("Remicade" sold by Mitsubishi Tanabe Pharma Corporation) was evaluated. The IgG-Fab was prepared in a similar manner to the above-described (1), and the affinity was basically evaluated in a similar manner to the above-described (2). However, the concentrations of the peptide solutions were adjusted to 25 nM, 100 nM or 400 nM. The analysis result is shown in Table 2.

TABLE 2

| Sequence number | | Anti-EGFR antibody - Fab | | | Anti-TNFα antibody - Fab | | |
|---|---|---|---|---|---|---|---|
| | | $k_{on}$ | $k_{off}$ | $K_A$ | $k_{on}$ | $k_{off}$ | $K_A$ |
| Amino acid sequence | cDNA sequence | ×10$^4$ M$^{-1}$s | ×10$^{-2}$ s$^{-1}$ | ×10$^6$ M$^{-1}$ | ×10$^4$ M$^{-1}$s | ×10$^{-2}$ s$^{-1}$ | ×10$^6$ M$^{-1}$ |
| 2 | 3 | 25.2 | 3.9 | 65.0 | 41.3 | 1.0 | 40.0 |

As the result shown in Table 2, it was confirmed that the peptide can bind to other IgG-Fab in an association constant of the same order. From the above result, the peptide is considered to bind to Fab at a site different from antigen-binding site but in a similar manner. The above-described two antibodies are chimeric antibodies and have the IgG-Fab which is derived from subfamily V of mouse VL$_K$ and to which Protein L hardly binds. Thus, the result can be considered to be data to demonstrate that the peptide according to the present invention exhibits a high versatility.

Example 3

Preparation and Evaluation of IgG-Binding Peptide

With respect to the peptides according to the present invention having sequences different from SEQ ID NO: 2, respective peptide was prepared and the binding performance thereof was evaluated. The sequence of the IgG-binding peptide and the sequence of the peptide-coding DNA and the expression plasmid used in the present Example are shown in the following Table.

TABLE 3

| IgG-binding peptide | | | Preparation of expression plasmid | | | |
|---|---|---|---|---|---|---|
| Sequence number | | Difference from amino acid sequence of SEQ ID NO: 2 | SEQ ID NO of single-stranded oligo DNA | | | |
| Amino acid | cDNA | | f1-1 | f1-2 | f2-1 | f2-2 |
| 9 | 18 | Xaa$_{10}$ = Arg | 27 | 5 | 6 | 7 |
| 10 | 19 | Xaa$_{21}$ = Asp | 4 | 28 | 6 | 7 |
| 11 | 20 | Xaa$_{28}$ = Lys | 4 | 5 | 29 | 7 |
| 12 | 21 | Xaa$_{39}$ = Val | 4 | 5 | 30 | 7 |
| 13 | 22 | Xaa$_{47}$ = Ala | 4 | 5 | 6 | 31 |
| 14 | 23 | Xaa$_{21}$ = Asp, Xaa$_{28}$ = Lys | 4 | 28 | 29 | 7 |
| 15 | 24 | Xaa$_{21}$ = Asp, Xaa$_{47}$ = Ala | 4 | 28 | 6 | 31 |
| 16 | 25 | Xaa$_{28}$ = Lys, Xaa$_{47}$ = Ala | 4 | 5 | 29 | 31 |
| 17 | 26 | Xaa$_{21}$ = Asp, Xaa$_{28}$ = Lys, Xaa$_{47}$ = Ala | 4 | 28 | 29 | 31 |

Each peptide was prepared in a similar method to the above-described Example 1 except that the combination of single-stranded oligo DNAs shown in Table 3 was used for preparing expression plasmid. It was confirmed that the prepared peptide has approximately similar binding performance to IgG-Fab/Fc. As representative data, the affinity for IgG-Fab of anti-TNFα monoclonal antibody was evaluated by a similar manner to the above-described Example 2. The parameter of the peptide having SEQ ID NO: 2 was measured again, and the result is demonstrated as a graph of FIG. 2 in the form of the comparison of each binding parameter with the remeasurement parameter of the peptide having SEQ ID NO: 2. For example, the value in the left graph is logarithm (Log 10) of a value calculated by dividing an affinity constant ($K_A$) of each peptide by an affinity constant of SEQ ID NO: 2. When the logarithm value is 0, both affinity constants are the same; when an affinity constant is 10 times larger, the logarithm value is 1; and when an affinity constant is 1/10 times, the logarithm value is −1. Similarly, an association rate constant ($k_{on}$) and a dissociation rate constant ($k_{off}$) are also demonstrated. Since a smaller dissociation rate constant indicates a better result, the horizontal axis of a dissociation rate constant graph is inverted. As a result, the absolute values of each peptide in the graphs are about 0.3 at most. In other words, binding parameters of each peptide are included in the range of about 0.5 to 2 times to a binding parameter of the peptide having SEQ ID NO: 2. It is demonstrated from the result that the above IgG-binding peptides are excellent in binding capability to IgG.

Comparative Example 1

Preparation of IgG-Binding Peptide Having Sequence of Protein G β1 Domain

A base sequence (SEQ ID NO: 33) encoding the peptide having the amino acid sequence of β1 domain of Protein G (SEQ ID NO: 32) was designed by reverse translation from the amino acid sequence in a similar manner to the above Example 1. In the amino acid sequence, the 1$^{st}$ position was Thr for experimental reason. The title peptide was prepared in a similar method to the above Example 1 except that single-stranded oligo DNAs used for preparing an expression plasmid were f1-1 (SEQ ID NO: 34), f1-2 (SEQ ID NO: 35) and f2-1 (SEQ ID NO: 36). The peptide was used as a comparative sample in the following Example 4.

Example 4

Evaluation of Potential as Peptide for Measuring Concentration

A sensor tip was prepared by immobilizing the IgG-Fc/Fab of anti-TNFα monoclonal antibody on separate lanes so that the immobilized amount became about 10000 RU in a similar manner to the above Example 2(2). By using the sensor tip, in a similar manner to the above Example 2(2), peptide solutions of the IgG-binding peptide of SEQ ID NO: 14 having concentration of 25 nM, 50 nM, 100 nM or 200 nM flowed at a rate of 10 μL/min across the sensor tip, and the binding response (resonance unit value) was measured 1 minute after the addition. In FIG. 3, binding responses are plotted on the vertical axis and peptide concentrations are plotted on the horizontal axis. The result of the case where a binding partner was IgG-Fc is demonstrated as FIG. 3(1), and the result of the case where a binding partner was IgG-Fab is demonstrated as FIG. 3(2). In addition, the data of the case where peptide having the sequence of the β1 domain of publicly-known wild Protein G prepared in the above Comparative Example 1 (SEQ ID NO: 32) is also demonstrated.

As the result shown in FIG. 3, there is a linear correlation between peptide concentration and binding response. The approximate expressions of primary approximate curves are also demonstrated in FIG. 3. The inclinations of the approximate curves of the peptide having SEQ ID NO: 14 are about 0.5, specifically 0.4 to 0.6, in both cases of IgG-Fc and IgG-Fab. On the one hand, with respect to the peptide of the above Comparative Example, the inclination is about 0.9 in the case of IgG-Fc but the inclination is about 0.1 in the case of Fab. Since the binding forces of the present invention peptide to Fc and Fab are similar to each other, the inclinations in both cases are also similar to each other. In biochemical assay using binding amount to a target molecular as an index, a calibration curve is prepared using a sample having a known concentration as demonstrated in FIG. 3, a binding amount of a sample having unknown concentration is measured, and the concentration of the sample having unknown concentration is estimated using the calibration curve. Not only the peptide according to the present invention can bind to both IgG-Fc and IgG-Fab which are widely utilized in immunological assay or the like but also the binding forces thereof to the both regions are similar to each other as the above-described experimental result, and thus the inclinations of the calibration curves are also similar to each other. In such a way, since similar signals are measured in both cases of IgG-Fc and IgG-Fab as partner molecules for the measurement, it is not needed as an advantage to respectively customize measurement systems.

The invention claimed is:

1. An immunoglobulin G-binding peptide, comprising the following amino acid sequence (SEQ ID NO: 1) or an amino acid sequence having a sequence identity of 95% or more with the following amino acid sequence:

(SEQ ID NO: 1)
$Xaa_1$-$Xaa_2$-Tyr-Lys-Leu-$Xaa_6$-$Xaa_7$-Asn-Gly-$Xaa_{10}$-Thr-
Leu-Thr-Gly-Tyr-Thr-Thr-Ala-Ile-Ala-$Xaa_{21}$-Asp-Ala-
$Xaa_{24}$-Thr-Ala-Glu-$Xaa_{28}$-$Xaa_{29}$-Leu-$Xaa_{31}$-Gln-Phe-
Ala-Asn-Asp-Asn-Gly-$Xaa_{39}$-$Xaa_{40}$-Gly-$Xaa_{42}$-Trp-Thr-
Tyr-Asp-$Xaa_{47}$-Ala-Thr-Lys-Thr-Phe-Thr-Val-Thr-$Xaa_{56}$ wherein,
$Xaa_1$ is one of the following amino acids: Ala, Gly, Ile, Leu, Met, Asn, Gln, Ser, Thr, or Val;
$Xaa_2$ is Thr;
$Xaa_6$ is one of the following amino acids: Ile, or Val;
$Xaa_7$ is one of the following amino acids: Leu, or Ile;
$Xaa_{10}$ is one of the following amino acids: Lys, or Arg;
$Xaa_{21}$ is one of the following amino acids: Asp, or Ala;
$Xaa_{24}$ is Ala;
$Xaa_{28}$ is one of the following amino acids: Lys, Ile, or Arg;
$Xaa_{29}$ is one of the following amino acids: Val, or Ala;
$Xaa_{31}$ is one of the following amino acids: Lys, or Arg;
$Xaa_{39}$ is one of the following amino acids: Val, or Ile;
$Xaa_{40}$ is one of the following amino acids: Asp, or Glu;
$Xaa_{42}$ is Glu;
$Xaa_{47}$ is one of the following amino acids: Asp, or Ala; and
$Xaa_{56}$ is one of the following amino acids: Asp, or Glu.

2. The immunoglobulin G-binding peptide according to claim 1, wherein $Xaa_6$ is Ile.

3. The immunoglobulin G-binding peptide according to claim 1, wherein $Xaa_7$ is Leu.

4. The immunoglobulin G-binding peptide according to claim 1, wherein $Xaa_{29}$ is Val.

5. The immunoglobulin G-binding peptide according to claim 1, wherein $Xaa_{31}$ is Lys.

6. The immunoglobulin G-binding peptide according to claim 1, wherein $Xaa_{40}$ is Asp.

7. A DNA, encoding the peptide according to claim 1.

8. A vector, comprising the DNA according to claim 7.

9. A transformant, transformed by the vector according to claim 8.

10. The immunoglobulin G-binding peptide according to claim 1, wherein $Xaa_{10}$ is Arg.

11. The immunoglobulin G-binding peptide according to claim 1, wherein $Xaa_{21}$ is Asp.

12. The immunoglobulin G-binding peptide according to claim 1, wherein $Xaa_{28}$ is Lys.

13. The immunoglobulin G-binding peptide according to claim 1, wherein $Xaa_{39}$ is Val.

14. The immunoglobulin G-binding peptide according to claim 1, wherein $Xaa_{47}$ is Ala.

15. The immunoglobulin G-binding peptide according to claim 1, wherein $Xaa_1$ is Ser, Thr, or Ala.

16. The immunoglobulin G-binding peptide according to claim 1 wherein, the amino acid sequence is selected from the following amino acid sequences: SEQ ID NO:2, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO:17.

17. The immunoglobulin G-binding peptide according to claim 1 wherein,
$Xaa_1$ is one of the following amino acids: Thr, Ser, Asn, or Gln;
$Xaa_2$ is Thr;
$Xaa_6$ is one of the following amino acids: Ile, or Val;
$Xaa_7$ is one of the following amino acids: Leu, or Ile;
$Xaa_{10}$ is one of the following amino acids: Lys, or Arg;
$Xaa_{21}$ is one of the following amino acids: Asp, or Ala;
$Xaa_{24}$ is Ala;
$Xaa_{28}$ is one of the following amino acids: Lys, Ile, or Arg;
$Xaa_{29}$ is one of the following amino acids: Val, or Ala;
$Xaa_{31}$ is one of the following amino acids: Lys, or Arg;
$Xaa_{39}$ is one of the following amino acids: Val, or Ile;
$Xaa_{40}$ is one of the following amino acids: Asp, or Glu;
$Xaa_{42}$ is Glu;
$Xaa_{47}$ is one of the following amino acids: Asp, or Ala; and
$Xaa_{56}$ is one of the following amino acids: Asp, or Glu.

18. The immunoglobulin G-binding peptide according to claim 1 wherein,
$Xaa_1$ is Thr;
$Xaa_2$ is Thr;

$Xaa_6$ is Ile;
$Xaa_7$ is Leu;
$Xaa_{10}$ is one of the following amino acids: Lys, or Arg;
$Xaa_{21}$ is one of the following amino acids: Asp, or Ala;
$Xaa_{24}$ is Ala;
$Xaa_{28}$ is one of the following amino acids: Lys, or Ile;
$Xaa_{29}$ is Val;
$Xaa_{31}$ is Lys;
$Xaa_{39}$ is one of the following amino acids: Val, or Ile;
$Xaa_{40}$ is Asp;
$Xaa_{42}$ is Glu;
$Xaa_{47}$ is one of the following amino acids: Asp, or Ala; and
$Xaa_{56}$ is Glu.

19. The immunoglobulin G-binding peptide according to claim 1 wherein,
$Xaa_1$ is one of the following amino acids: Ala, Gly, Ile, Leu, Met, Asn, Gln, Ser, Thr, or Val;
$Xaa_2$ is Thr;
$Xaa_6$ is Ile;
$Xaa_7$ is Leu;
$Xaa_{10}$ is one of the following amino acids: Lys, or Arg;
$Xaa_{21}$ is one of the following amino acids: Asp, or Ala;
$Xaa_{24}$ is Ala;
$Xaa_{28}$ is one of the following amino acids: Lys, or Ile;
$Xaa_{29}$ is Val;
$Xaa_{31}$ is Lys;
$Xaa_{39}$ is one of the following amino acids: Val, or Ile;
$Xaa_{40}$ is Asp;
$Xaa_{42}$ is Glu;
$Xaa_{47}$ is one of the following amino acids: Asp, or Ala; and
$Xaa_{56}$ is Glu.

* * * * *

SEQUENCE LISTING

```
<160> NUMBER OF SEQ ID NOS: 37

<210> SEQ ID NO 1
<211> LENGTH: 56
<212> TYPE: PRT
<213> ORGANISM: Artificial Sequence
<220> FEATURE:
<223> OTHER INFORMATION: Artificial Peptide
<220> FEATURE:
<221> NAME/KEY: MISC_FEATURE
<222> LOCATION: (1)..(1)
<223> OTHER INFORMATION: Xaa at position 1 is Ala, Asp, Glu, Gly, His,
      Ile, Lys, Leu, Met, Asn, Gln, Arg, Ser, Thr or Val
<220> FEATURE:
<221> NAME/KEY: MISC_FEATURE
<222> LOCATION: (2)..(2)
<223> OTHER INFORMATION: Xaa at position 2 is Thr or Arg
<220> FEATURE:
<221> NAME/KEY: MISC_FEATURE
<222> LOCATION: (6)..(6)
<223> OTHER INFORMATION: Xaa at position 6 is Ile or Val
<220> FEATURE:
<221> NAME/KEY: MISC_FEATURE
<222> LOCATION: (7)..(7)
<223> OTHER INFORMATION: Xaa at position 7 is Leu or Ile
<220> FEATURE:
<221> NAME/KEY: MISC_FEATURE
<222> LOCATION: (10)..(10)
<223> OTHER INFORMATION: Xaa at position 10 is Lys or Arg
<220> FEATURE:
<221> NAME/KEY: MISC_FEATURE
<222> LOCATION: (21)..(21)
<223> OTHER INFORMATION: Xaa at position 21 is Asp, Ala or Pro
<220> FEATURE:
<221> NAME/KEY: MISC_FEATURE
<222> LOCATION: (24)..(24)
<223> OTHER INFORMATION: Xaa at position 24 is Ala or Glu
<220> FEATURE:
<221> NAME/KEY: MISC_FEATURE
<222> LOCATION: (28)..(28)
<223> OTHER INFORMATION: Xaa at position 28 is Lys, Ile or Arg
<220> FEATURE:
<221> NAME/KEY: MISC_FEATURE
<222> LOCATION: (29)..(29)
<223> OTHER INFORMATION: Xaa at position 29 is Val or Ala
<220> FEATURE:
<221> NAME/KEY: MISC_FEATURE
<222> LOCATION: (31)..(31)
<223> OTHER INFORMATION: Xaa at position 31 is Lys or Arg
<220> FEATURE:
<221> NAME/KEY: MISC_FEATURE
<222> LOCATION: (39)..(39)
<223> OTHER INFORMATION: Xaa at position 39 is Val or Ile
<220> FEATURE:
<221> NAME/KEY: MISC_FEATURE
<222> LOCATION: (40)..(40)
```

```
<223> OTHER INFORMATION: Xaa at position 40 is Asp or Glu
<220> FEATURE:
<221> NAME/KEY: MISC_FEATURE
<222> LOCATION: (42)..(42)
<223> OTHER INFORMATION: Xaa at position 42 is Glu, Val or Met
<220> FEATURE:
<221> NAME/KEY: MISC_FEATURE
<222> LOCATION: (47)..(47)
<223> OTHER INFORMATION: Xaa at position 47 is Asp, Ala or Pro
<220> FEATURE:
<221> NAME/KEY: MISC_FEATURE
<222> LOCATION: (56)..(56)
<223> OTHER INFORMATION: Xaa at position 56 is Ala, Asp, Glu, Gly, His,
      Ile, Lys, Leu, Met, Asn, Gln, Arg, Ser, Thr or Val

<400> SEQUENCE: 1

Xaa Xaa Tyr Lys Leu Xaa Xaa Asn Gly Xaa Thr Leu Thr Gly Tyr Thr
1               5                   10                  15

Thr Ala Ile Ala Xaa Asp Ala Xaa Thr Ala Glu Xaa Xaa Leu Xaa Gln
            20                  25                  30

Phe Ala Asn Asp Asn Gly Xaa Xaa Gly Xaa Trp Thr Tyr Asp Xaa Ala
        35                  40                  45

Thr Lys Thr Phe Thr Val Thr Xaa
    50                  55

<210> SEQ ID NO 2
<211> LENGTH: 56
<212> TYPE: PRT
<213> ORGANISM: Artificial Sequence
<220> FEATURE:
<223> OTHER INFORMATION: Immunoglobulin-binding peptide

<400> SEQUENCE: 2

Thr Thr Tyr Lys Leu Ile Leu Asn Gly Lys Thr Leu Thr Gly Tyr Thr
1               5                   10                  15

Thr Ala Ile Ala Ala Asp Ala Ala Thr Ala Glu Ile Val Leu Lys Gln
            20                  25                  30

Phe Ala Asn Asp Asn Gly Ile Asp Gly Glu Trp Thr Tyr Asp Asp Ala
        35                  40                  45

Thr Lys Thr Phe Thr Val Thr Glu
    50                  55

<210> SEQ ID NO 3
<211> LENGTH: 171
<212> TYPE: DNA
<213> ORGANISM: Artificial Sequence
<220> FEATURE:
<223> OTHER INFORMATION: Immunoglobulin-binding peptide code DNA

<400> SEQUENCE: 3
accacctaca aactgatcct gaacggtaag accctgacag gttacaccac cgccatagct      60
gctgacgctg ctacggccga aattgtgctc aaacagttcg ctaacgacaa cggtatcgac     120
ggtgaatgga cctacgacga cgctaccaaa accttcacgg ttaccgaata a              171

<210> SEQ ID NO 4
<211> LENGTH: 57
<212> TYPE: DNA
<213> ORGANISM: Artificial Sequence
<220> FEATURE:
<223> OTHER INFORMATION: Synthetic: oligo DNA

<400> SEQUENCE: 4
cgtggatcca ccacctacaa actgatcctg aacggtaaga ccctgacagg ttacacc         57
```

-continued

```
<210> SEQ ID NO 5
<211> LENGTH: 45
<212> TYPE: DNA
<213> ORGANISM: Artificial Sequence
<220> FEATURE:
<223> OTHER INFORMATION: Synthetic: oligo DNA

<400> SEQUENCE: 5
aatttcggcc gtagcagcgt cagcagctat ggcggtggtg taacc              45

<210> SEQ ID NO 6
<211> LENGTH: 60
<212> TYPE: DNA
<213> ORGANISM: Artificial Sequence
<220> FEATURE:
<223> OTHER INFORMATION: Synthetic: oligo DNA

<400> SEQUENCE: 6
gctacggccg aaattgtgct caaacagttc gctaacgaca acggtatcga cggtgaatgg    60

<210> SEQ ID NO 7
<211> LENGTH: 60
<212> TYPE: DNA
<213> ORGANISM: Artificial Sequence
<220> FEATURE:
<223> OTHER INFORMATION: Synthetic: oligo DNA

<400> SEQUENCE: 7
gatgaattct tattcggtaa ccgtgaaggt tttggtagcg tcgtcgtagg tccattcacc    60

<210> SEQ ID NO 8
<211> LENGTH: 56
<212> TYPE: PRT
<213> ORGANISM: Artificial Sequence
<220> FEATURE:
<223> OTHER INFORMATION: Articficial Peptide
<220> FEATURE:
<221> NAME/KEY: MISC_FEATURE
<222> LOCATION: (1)..(1)
<223> OTHER INFORMATION: Xaa at position 1 is Ala, Asp, Glu, Gly, His,
      Ile, Lys, Leu, Met, Asn, Gln, Arg, Ser, Thr or Val
<220> FEATURE:
<221> NAME/KEY: MISC_FEATURE
<222> LOCATION: (10)..(10)
<223> OTHER INFORMATION: Xaa at position 10 is Lys or Arg
<220> FEATURE:
<221> NAME/KEY: MISC_FEATURE
<222> LOCATION: (21)..(21)
<223> OTHER INFORMATION: Xaa at position 21 is Asp or Ala
<220> FEATURE:
<221> NAME/KEY: MISC_FEATURE
<222> LOCATION: (28)..(28)
<223> OTHER INFORMATION: Xaa at position 28 is Lys or Ile
<220> FEATURE:
<221> NAME/KEY: MISC_FEATURE
<222> LOCATION: (39)..(39)
<223> OTHER INFORMATION: Xaa at position 39 is Val or Ile
<220> FEATURE:
<221> NAME/KEY: MISC_FEATURE
<222> LOCATION: (47)..(47)
<223> OTHER INFORMATION: Xaa at position 47 is Asp or Ala
<220> FEATURE:
<221> NAME/KEY: MISC_FEATURE
<222> LOCATION: (56)..(56)
<223> OTHER INFORMATION: Xaa at position 56 is Ala, Asp, Glu, Gly, His,
      Ile, Lys, Leu, Met, Asn, Gln, Arg, Ser, Thr or Val

<400> SEQUENCE: 8

Xaa Thr Tyr Lys Leu Ile Leu Asn Gly Xaa Thr Leu Thr Gly Tyr Thr
1               5                   10                  15
```

Thr Ala Ile Ala Xaa Asp Ala Ala Thr Ala Glu Xaa Val Leu Lys Gln
            20                  25                  30

Phe Ala Asn Asp Asn Gly Xaa Asp Gly Glu Trp Thr Tyr Asp Xaa Ala
        35                  40                  45

Thr Lys Thr Phe Thr Val Thr Xaa
    50                  55

<210> SEQ ID NO 9
<211> LENGTH: 56
<212> TYPE: PRT
<213> ORGANISM: Artificial Sequence
<220> FEATURE:
<223> OTHER INFORMATION: Immunoglobulin-binding peptide

<400> SEQUENCE: 9

Thr Thr Tyr Lys Leu Ile Leu Asn Gly Arg Thr Leu Thr Gly Tyr Thr
1               5                   10                  15

Thr Ala Ile Ala Ala Asp Ala Ala Thr Ala Glu Ile Val Leu Lys Gln
            20                  25                  30

Phe Ala Asn Asp Asn Gly Ile Asp Gly Glu Trp Thr Tyr Asp Asp Ala
        35                  40                  45

Thr Lys Thr Phe Thr Val Thr Glu
    50                  55

<210> SEQ ID NO 10
<211> LENGTH: 56
<212> TYPE: PRT
<213> ORGANISM: Artificial Sequence
<220> FEATURE:
<223> OTHER INFORMATION: Immunoglobulin-binding peptide

<400> SEQUENCE: 10

Thr Thr Tyr Lys Leu Ile Leu Asn Gly Lys Thr Leu Thr Gly Tyr Thr
1               5                   10                  15

Thr Ala Ile Ala Asp Asp Ala Thr Ala Glu Ile Val Leu Lys Gln
            20                  25                  30

Phe Ala Asn Asp Asn Gly Ile Asp Gly Glu Trp Thr Tyr Asp Asp Ala
        35                  40                  45

Thr Lys Thr Phe Thr Val Thr Glu
    50                  55

<210> SEQ ID NO 11
<211> LENGTH: 56
<212> TYPE: PRT
<213> ORGANISM: Artificial Sequence
<220> FEATURE:
<223> OTHER INFORMATION: Immunoglobulin-binding peptide

<400> SEQUENCE: 11

Thr Thr Tyr Lys Leu Ile Leu Asn Gly Lys Thr Leu Thr Gly Tyr Thr
1               5                   10                  15

Thr Ala Ile Ala Ala Asp Ala Ala Thr Ala Glu Lys Val Leu Lys Gln
            20                  25                  30

Phe Ala Asn Asp Asn Gly Ile Asp Gly Glu Trp Thr Tyr Asp Asp Ala
        35                  40                  45

Thr Lys Thr Phe Thr Val Thr Glu
    50                  55

<210> SEQ ID NO 12
<211> LENGTH: 56
<212> TYPE: PRT

<210> SEQ ID NO 13
<211> LENGTH: 56
<212> TYPE: PRT
<213> ORGANISM: Artificial Sequence
<220> FEATURE:
<223> OTHER INFORMATION: Immunoglobulin-binding peptide

<400> SEQUENCE: 12

Thr Thr Tyr Lys Leu Ile Leu Asn Gly Lys Thr Leu Thr Gly Tyr Thr
1               5                   10                  15

Thr Ala Ile Ala Ala Asp Ala Ala Thr Ala Glu Ile Val Leu Lys Gln
            20                  25                  30

Phe Ala Asn Asp Asn Gly Val Asp Gly Glu Trp Thr Tyr Asp Asp Ala
        35                  40                  45

Thr Lys Thr Phe Thr Val Thr Glu
    50                  55

<210> SEQ ID NO 13
<211> LENGTH: 56
<212> TYPE: PRT
<213> ORGANISM: Artificial Sequence
<220> FEATURE:
<223> OTHER INFORMATION: Immunoglobulin-binding peptide

<400> SEQUENCE: 13

Thr Thr Tyr Lys Leu Ile Leu Asn Gly Lys Thr Leu Thr Gly Tyr Thr
1               5                   10                  15

Thr Ala Ile Ala Ala Asp Ala Ala Thr Ala Glu Ile Val Leu Lys Gln
            20                  25                  30

Phe Ala Asn Asp Asn Gly Ile Asp Gly Glu Trp Thr Tyr Asp Ala Ala
        35                  40                  45

Thr Lys Thr Phe Thr Val Thr Glu
    50                  55

<210> SEQ ID NO 14
<211> LENGTH: 56
<212> TYPE: PRT
<213> ORGANISM: Artificial Sequence
<220> FEATURE:
<223> OTHER INFORMATION: Immunoglobulin-binding peptide

<400> SEQUENCE: 14

Thr Thr Tyr Lys Leu Ile Leu Asn Gly Lys Thr Leu Thr Gly Tyr Thr
1               5                   10                  15

Thr Ala Ile Ala Asp Asp Ala Ala Thr Ala Glu Lys Val Leu Lys Gln
            20                  25                  30

Phe Ala Asn Asp Asn Gly Ile Asp Gly Glu Trp Thr Tyr Asp Asp Ala
        35                  40                  45

Thr Lys Thr Phe Thr Val Thr Glu
    50                  55

<210> SEQ ID NO 15
<211> LENGTH: 56
<212> TYPE: PRT
<213> ORGANISM: Artificial Sequence
<220> FEATURE:
<223> OTHER INFORMATION: Immunoglobulin-binding peptide

<400> SEQUENCE: 15

Thr Thr Tyr Lys Leu Ile Leu Asn Gly Lys Thr Leu Thr Gly Tyr Thr
1               5                   10                  15

Thr Ala Ile Ala Asp Asp Ala Ala Thr Ala Glu Ile Val Leu Lys Gln
            20                  25                  30

Phe Ala Asn Asp Asn Gly Ile Asp Gly Glu Trp Thr Tyr Asp Ala Ala
        35                  40                  45

```
                   35                  40                  45

Thr Lys Thr Phe Thr Val Thr Glu
         50                  55

<210> SEQ ID NO 16
<211> LENGTH: 56
<212> TYPE: PRT
<213> ORGANISM: Artificial Sequence
<220> FEATURE:
<223> OTHER INFORMATION: Immunoglobulin-binding peptide

<400> SEQUENCE: 16

Thr Thr Tyr Lys Leu Ile Leu Asn Gly Lys Thr Leu Thr Gly Tyr Thr
1               5                  10                  15

Thr Ala Ile Ala Ala Asp Ala Ala Thr Ala Glu Lys Val Leu Lys Gln
            20                  25                  30

Phe Ala Asn Asp Asn Gly Ile Asp Gly Glu Trp Thr Tyr Asp Ala Ala
        35                  40                  45

Thr Lys Thr Phe Thr Val Thr Glu
         50                  55

<210> SEQ ID NO 17
<211> LENGTH: 56
<212> TYPE: PRT
<213> ORGANISM: Artificial Sequence
<220> FEATURE:
<223> OTHER INFORMATION: Immunoglobulin-binding peptide

<400> SEQUENCE: 17

Thr Thr Tyr Lys Leu Ile Leu Asn Gly Lys Thr Leu Thr Gly Tyr Thr
1               5                  10                  15

Thr Ala Ile Ala Asp Asp Ala Ala Thr Ala Glu Lys Val Leu Lys Gln
            20                  25                  30

Phe Ala Asn Asp Asn Gly Ile Asp Gly Glu Trp Thr Tyr Asp Ala Ala
        35                  40                  45

Thr Lys Thr Phe Thr Val Thr Glu
         50                  55

<210> SEQ ID NO 18
<211> LENGTH: 168
<212> TYPE: DNA
<213> ORGANISM: Artificial Sequence
<220> FEATURE:
<223> OTHER INFORMATION: Artificial peptide cDNA

<400> SEQUENCE: 18
accacctaca aactgatcct gaacggacgt accctgacag gttacaccac cgccatagct      60
gctgacgctg ctacggccga aattgtgctc aaacagttcg ctaacgacaa cggtatcgac     120
ggtgaatgga cctacgacga cgctaccaaa accttcacgg ttaccgaa                  168

<210> SEQ ID NO 19
<211> LENGTH: 168
<212> TYPE: DNA
<213> ORGANISM: Artificial Sequence
<220> FEATURE:
<223> OTHER INFORMATION: Immunoglobulin-binding peptide code DNA

<400> SEQUENCE: 19
accacctaca aactgatcct gaacggaaag accctgacag gttacaccac cgccatagct      60
gatgacgctg ctacggccga aattgtgctc aaacagttcg ctaacgacaa cggtatcgac     120
```
ggtgaatgga cctacgacga cgctaccaaa accttcacgg ttaccgaa          168

<210> SEQ ID NO 20
<211> LENGTH: 168
<212> TYPE: DNA
<213> ORGANISM: Artificial Sequence
<220> FEATURE:
<223> OTHER INFORMATION: Immunoglobulin-binding peptide code DNA

<400> SEQUENCE: 20
accacctaca aactgatcct gaacggaaag accctgacag gttacaccac cgccatagct   60
gctgacgctg ctacggccga aaaggtgctc aaacagttcg ctaacgacaa cggtatcgac  120
ggtgaatgga cctacgacga cgctaccaaa accttcacgg ttaccgaa          168

<210> SEQ ID NO 21
<211> LENGTH: 168
<212> TYPE: DNA
<213> ORGANISM: Artificial Sequence
<220> FEATURE:
<223> OTHER INFORMATION: Immunoglobulin-binding peptide code DNA

<400> SEQUENCE: 21
accacctaca aactgatcct gaacggaaag accctgacag gttacaccac cgccatagct   60
gctgacgctg ctacggccga aattgtgctc aaacagttcg ctaacgacaa cggtgtcgac  120
ggtgaatgga cctacgacga cgctaccaaa accttcacgg ttaccgaa          168

<210> SEQ ID NO 22
<211> LENGTH: 168
<212> TYPE: DNA
<213> ORGANISM: Artificial Sequence
<220> FEATURE:
<223> OTHER INFORMATION: Immunoglobulin-binding peptide code DNA

<400> SEQUENCE: 22
accacctaca aactgatcct gaacggaaag accctgacag gttacaccac cgccatagct   60
gctgacgctg ctacggccga aattgtgctc aaacagttcg ctaacgacaa cggtatcgac  120
ggtgaatgga cctacgacgc cgctaccaaa accttcacgg ttaccgaa          168

<210> SEQ ID NO 23
<211> LENGTH: 168
<212> TYPE: DNA
<213> ORGANISM: Artificial Sequence
<220> FEATURE:
<223> OTHER INFORMATION: Immunoglobulin-binding peptide code DNA

<400> SEQUENCE: 23
accacctaca aactgatcct gaacggaaag accctgacag gttacaccac cgccatagct   60
gatgacgctg ctacggccga aaaggtgctc aaacagttcg ctaacgacaa cggtatcgac  120
ggtgaatgga cctacgacga cgctaccaaa accttcacgg ttaccgaa          168

<210> SEQ ID NO 24
<211> LENGTH: 168
<212> TYPE: DNA
<213> ORGANISM: Artificial Sequence
<220> FEATURE:
<223> OTHER INFORMATION: Immunoglobulin-binding peptide code DNA

<400> SEQUENCE: 24
accacctaca aactgatcct gaacggaaag accctgacag gttacaccac cgccatagct   60
gatgacgctg ctacggccga aattgtgctc aaacagttcg ctaacgacaa cggtatcgac  120
ggtgaatgga cctacgacgc cgctaccaaa accttcacgg ttaccgaa         168

<210> SEQ ID NO 25
<211> LENGTH: 168
<212> TYPE: DNA
<213> ORGANISM: Artificial Sequence
<220> FEATURE:
<223> OTHER INFORMATION: Immunoglobulin-binding peptide code DNA

<400> SEQUENCE: 25
accacctaca aactgatcct gaacggaaag accctgacag gttacaccac cgccatagct    60
gctgacgctg ctacggccga aaaggtgctc aaacagttcg ctaacgacaa cggtatcgac   120
ggtgaatgga cctacgacgc cgctaccaaa accttcacgg ttaccgaa                168

<210> SEQ ID NO 26
<211> LENGTH: 168
<212> TYPE: DNA
<213> ORGANISM: Artificial Sequence
<220> FEATURE:
<223> OTHER INFORMATION: Immunoglobulin-binding peptide code DNA

<400> SEQUENCE: 26
accacctaca aactgatcct gaacggaaag accctgacag gttacaccac cgccatagct    60
gatgacgctg ctacggccga aaaggtgctc aaacagttcg ctaacgacaa cggtatcgac   120
ggtgaatgga cctacgacgc cgctaccaaa accttcacgg ttaccgaa                168

<210> SEQ ID NO 27
<211> LENGTH: 57
<212> TYPE: DNA
<213> ORGANISM: Artificial Sequence
<220> FEATURE:
<223> OTHER INFORMATION: Synthetic: oligo DNA

<400> SEQUENCE: 27
cgtggatcca ccacctacaa actgatcctg aacggtcgta ccctgacagg ttacacc       57

<210> SEQ ID NO 28
<211> LENGTH: 45
<212> TYPE: DNA
<213> ORGANISM: Artificial Sequence
<220> FEATURE:
<223> OTHER INFORMATION: Synthetic: oligo DNA

<400> SEQUENCE: 28
aatttcggcc gtagcagcgt catcagctat ggcggtggtg taacc                    45

<210> SEQ ID NO 29
<211> LENGTH: 60
<212> TYPE: DNA
<213> ORGANISM: Artificial Sequence
<220> FEATURE:
<223> OTHER INFORMATION: Synthetic: oligo DNA

<400> SEQUENCE: 29
gctacggccg aaaaggtgct caaacagttc gctaacgaca acggtatcga cggtgaatgg    60

<210> SEQ ID NO 30
<211> LENGTH: 60
<212> TYPE: DNA
<213> ORGANISM: Artificial Sequence
<220> FEATURE:
<223> OTHER INFORMATION: Synthetic: oligo DNA

```
<400> SEQUENCE: 30
gctacggccg aaattgtgct caaacagttc gctaacgaca acggtgtcga cggtgaatgg    60

<210> SEQ ID NO 31
<211> LENGTH: 60
<212> TYPE: DNA
<213> ORGANISM: Artificial Sequence
<220> FEATURE:
<223> OTHER INFORMATION: Synthetic: oligo DNA

<400> SEQUENCE: 31
gatgaattct tattcggtaa ccgtgaaggt tttggtagcg gcgtcgtagg tccattcacc    60

<210> SEQ ID NO 32
<211> LENGTH: 56
<212> TYPE: PRT
<213> ORGANISM: Streptococcus mutans

<400> SEQUENCE: 32

Thr Thr Tyr Lys Leu Ile Leu Asn Gly Lys Thr Leu Lys Gly Glu Thr
  1               5                  10                  15

Thr Thr Glu Ala Val Asp Ala Ala Thr Ala Glu Lys Val Phe Lys Gln
             20                  25                  30

Tyr Ala Asn Asp Asn Gly Val Asp Gly Glu Trp Thr Tyr Asp Asp Ala
         35                  40                  45

Thr Lys Thr Phe Thr Val Thr Glu
     50                  55

<210> SEQ ID NO 33
<211> LENGTH: 168
<212> TYPE: DNA
<213> ORGANISM: Artificial Sequence
<220> FEATURE:
<223> OTHER INFORMATION: SpG-B1 code DNA

<400> SEQUENCE: 33
accacctaca aactgatcct gaacggtaag accctgaaag gtgaaaccac caccgaagct    60
gttgacgctg ctacggccga aaaagtgttc aaacagtacg ctaacgacaa cggtgtcgac   120
ggtgaatgga cctacgacga cgctaccaaa accttcacgg ttaccgaa               168

<210> SEQ ID NO 34
<211> LENGTH: 57
<212> TYPE: DNA
<213> ORGANISM: Artificial Sequence
<220> FEATURE:
<223> OTHER INFORMATION: Synthetic: oligo DNA

<400> SEQUENCE: 34
cgtggatcca ccacctacaa actgatcctg aacggtaaga ccctgaaagg tgaaacc       57

<210> SEQ ID NO 35
<211> LENGTH: 45
<212> TYPE: DNA
<213> ORGANISM: Artificial Sequence
<220> FEATURE:
<223> OTHER INFORMATION: Synthetic: oligo DNA

<400> SEQUENCE: 35
cttttcggcc gtagcagcgt caacagcttc ggtggtggtt tcacc                    45

<210> SEQ ID NO 36
<211> LENGTH: 60
```

```
<212> TYPE: DNA
<213> ORGANISM: Artificial Sequence
<220> FEATURE:
<223> OTHER INFORMATION: Synthetic: oligo DNA

<400> SEQUENCE: 36
gctacggccg aaaaagtgtt caaacagtac gctaacgaca acggtgtcga cggtgaatgg    60

<210> SEQ ID NO 37
<211> LENGTH: 5
<212> TYPE: PRT
<213> ORGANISM: Artificial Sequence
<220> FEATURE:
<223> OTHER INFORMATION: Synthetic peptide

<400> SEQUENCE: 37

Gly Pro Leu Gly Ser
1               5
```